United States Patent
Kostinko et al.

[11] Patent Number: 6,074,629
[45] Date of Patent: Jun. 13, 2000

[54] DENTIFRICE WITH A DYE ABSORBING SILICA FOR IMPARTING A SPECKLED APPEARANCE THERETO

[75] Inventors: John Kostinko, Bel Air; James Sumpter, Aberdeen; Kathleen S. Pike, Bel Air, all of Md.

[73] Assignee: J. M. Huber Corporation, Edison, N.J.

[21] Appl. No.: 09/123,196

[22] Filed: Jul. 27, 1998

[51] Int. Cl.[7] .................................................. A61K 7/16
[52] U.S. Cl. ............................................................ 424/49
[58] Field of Search ........................................ 424/49–88

[56] References Cited

U.S. PATENT DOCUMENTS

| | | | |
|---|---|---|---|
| Re. 29,634 | 5/1978 | Roberts, IV et al. | 424/57 |
| 3,574,823 | 4/1971 | Roberts, I et al. | 424/49 |
| 3,716,388 | 2/1973 | Lopez et al. | 106/289 |
| 3,728,446 | 4/1973 | Roberts et al. | 424/49 |
| 3,767,791 | 10/1973 | Cordon, I et al. | 424/49 |
| 3,803,301 | 4/1974 | Cordon, II et al. | 424/49 |
| 3,919,409 | 11/1975 | Perla et al. . | |
| 3,928,555 | 12/1975 | Gault . | |
| 3,929,987 | 12/1975 | Colodney et al. . | |
| 3,935,306 | 1/1976 | Roberts, II et al. | 424/49 |
| 3,955,942 | 5/1976 | Cordon, III et al. | 51/295 |
| 4,002,732 | 1/1977 | Gault . | |
| 4,003,971 | 1/1977 | Mannara . | |
| 4,069,311 | 1/1978 | Mannara . | |
| 4,069,312 | 1/1978 | Mannara . | |
| 4,089,943 | 5/1978 | Roberts, III et al. | 424/49 |
| 4,090,887 | 5/1978 | Marqvisee et al. | 106/288 |
| 4,132,560 | 1/1979 | Marqvisee et al. | 106/288 |
| 4,132,562 | 1/1979 | Burke, I et al. | 106/308 |
| 4,132,564 | 1/1979 | Burke, II et al. | 106/308 |
| 4,154,621 | 5/1979 | Burke, III et al. | 106/308 |
| 4,167,422 | 9/1979 | Bellanca et al. | 106/289 |
| 4,223,003 | 9/1980 | Scheller | 424/7 |
| 4,368,089 | 1/1983 | Smith . | |
| 4,376,762 | 3/1983 | Hauschild et al. . | |
| 4,376,763 | 3/1983 | Barth et al. . | |
| 4,405,399 | 9/1983 | Gibbons . | |
| 4,440,877 | 4/1984 | Hauschild et al. . | |
| 4,443,564 | 4/1984 | Hauschild et al. . | |
| 4,444,570 | 4/1984 | Barth et al. . | |
| 4,444,746 | 4/1984 | Harvey et al. | 424/49 |
| 4,467,921 | 8/1984 | Groonland et al. | 424/49 |
| 4,566,908 | 1/1986 | Nakatani et al. | 106/308 |
| 4,663,152 | 5/1987 | Barth et al. . | |
| 4,877,451 | 10/1989 | Winnik et al. | 106/23 |
| 5,074,917 | 12/1991 | Persello | 106/436 |
| 5,286,478 | 2/1994 | Persello . | |
| 5,318,628 | 6/1994 | Matijevic, I et al. | 106/499 |
| 5,344,489 | 9/1994 | Matijevic, II et al. | 106/442 |
| 5,766,312 | 6/1998 | Furhmann et al. . | |
| 5,846,570 | 12/1998 | Barrow et al. | 424/53 |
| 5,871,872 | 2/1999 | Matijevic, III et al. | 430/7 |
| 5,876,701 | 3/1999 | Waas et al. | 424/49 |

FOREIGN PATENT DOCUMENTS 0 016 866 B1 12/1980 European Pat. Off. .
0 249 524 B1 12/1987 European Pat. Off. .

OTHER PUBLICATIONS

Spears et al J. Assoc. Public Anal 25(2):47–54 CA 108:203351(1988) Qualitative Analysis of Synthetic Colorings in Food (Synthetic Food Coloring Dyes Absorbed on Silica Gel), 1987.

Lehmann et al Seifen Oele Fete Wachse 111(6):167–164 CA 103:42389(1985) Identification of Dyes in Mouth and Toothcare Agents (Synthetic Food in Toothpastes & Mouthwashes Absorbed on Silica Gel).

*Primary Examiner*—Shep K. Rose
*Attorney, Agent, or Firm*—Carlos Nieves

[57] ABSTRACT

A dentifrice containing a dye absorbing silica which imparts a speckled appearance in toothpaste or gel formulations. The dye absorbing silica comprises silica granules which have a linseed oil absorption of at least about 150 cc/100 g, an average particle size of about 400 $\mu$m to about 600 $\mu$m, an attrition value of less than 30%, and a pH of about 6 to about 8.

20 Claims, 1 Drawing Sheet

DENTIFRICE WITH A DYE ABSORBING SILICA FOR IMPARTING A SPECKLED APPEARANCE THERETO

TECHNICAL FIELD

This invention relates to a dye absorbing amorphous silica for imparting a speckled appearance in a dentifrice and, more particularly, to such a silica which is adapted to absorb dyes from a dentifrice in order to provide an aesthetically pleasing effect.

BACKGROUND OF THE INVENTION

Toothpastes and gel formulations which include speckles are known in the art. Besides providing a pleasing aesthetic effect, the speckles can be used to enhance the cleaning and polishing functions of the dentifrice. The speckles are preferably a different color or shade than the base of the dentifrice so that they are visually perceptible. Some known speckles can be incorporated into transparent or translucent gel dentifrices without causing the gel base to cloud. From a marketing standpoint, it has been found to be desirable to package such speckle containing dentifrices in transparent or translucent containers so that the speckles can be viewed by consumers.

U.S. Pat. Nos. 4,376,762, 4,376,763, 4,440,877, 4,444,570, and 4,663,152 disclose the incorporation of functional agglomerated speckles into dentifrices. The speckles contain water insoluble powdered material and water insoluble, ethanol soluble ethyl cellulose. The powdered material is characterized as the functional bodying agent while the cellulose acts as a binder. The utilization of a binder has several short comings. By way of example, the binder material may dissolve in the toothpaste or gel, thereby causing the speckles to lose their integrity. Further, the addition of the binder increases the time and expense of producing the speckles. The use of an organic binder may also facilitate the growth of bacteria.

Several other patents disclose the incorporation of speckled particles into dentifrices. These patents include: U.S. Pat. Nos. 3,919,409, 3,928,555, 3,929,987, 4,002,732, 4,003,971, 4,069,311, and 4,069,312. In each of these patents an organic binder is utilized to bind the functional component of the speckled particles. As stated above, there are several drawbacks associated with the use of such a binder.

Moreover, existing speckles are not designed to absorb dyes from colored dentifrice formulations into which the speckles are incorporated. It is desirable for the silica particles to absorb dyes so that they will be readily discernible in the dentifrice. Such absorption produces an aesthetically pleasing effect. Heretofore, in order to incorporate colored speckles into a dentifrice, the speckles are typically dyed prior to being mixed into the formulation. This results in increased manufacturing time and cost.

SUMMARY OF THE INVENTION

The present invention is designed to overcome the deficiencies of the prior art discussed above. It is an object of the invention to provide a dye absorbing amorphous silica which imparts a speckled appearance in a dentifrice formulation to provide an aesthetically pleasing effect.

It is a further object of the invention to provide such a dye absorbing amorphous silica which is not susceptible to bacteria growth.

It is yet another object of the invention to provide a dye absorbing amorphous silica which maintains its integrity in dentifrice formulations.

In accordance with the illustrative embodiments and demonstrating features of the present invention, there is provided a dye absorbing amorphous silica which imparts a speckled appearance in a toothpaste or gel formulation. The dye absorbing silica comprises silica granules which have a linseed oil absorption of at least about 150 cc/100 g, an average particle size of about 400 $\mu$m to about 600 $\mu$m, an attrition value of less than 30%, and a pH of about 6 to about 8.

Other objects, features, and advantages will be readily apparent from the following detailed description of preferred embodiments thereof.

DETAILED DESCRIPTION OF PREFERRED EMBODIMENTS

Figure 1:
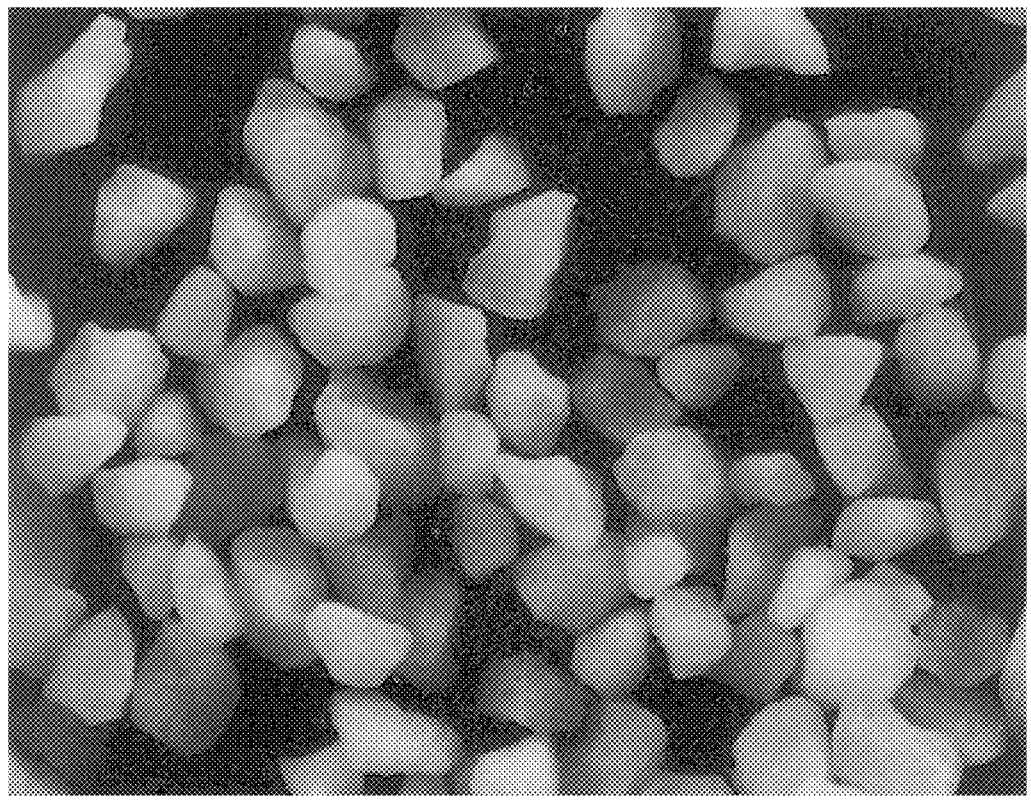
FIG. 1 is a photomicrograph of a dye absorbing silica granule (taken at 18×magnification) of the present invention.

In accordance with the preceding summary, the present invention is directed toward a dye absorbing silica which imparts a speckled appearance in a toothpaste or gel formulation. The dye absorbing silica comprises amorphous silica granules which preferably have a particle size of about 400 $\mu$m to about 600 $\mu$m. The particle size of the granules is significant. Specifically, if the granules are too small they become visually imperceptible and if the granules are too large they will produce an undesirable mouth feel.

In the preferred embodiment, the silica granules have a linseed oil absorption of at least about 150 cc/100 g and, more preferably, from about 165 to about 230 cc/100 g. The preferred attrition value is less than 30% and, more preferably, less than 20%. The preferred bulk density of the silica granules is about 0.2 g/ml to about 0.6 g/ml and the pH is about 6 to about 8.

The silica granules are preferably obtained in the following manner. Dried amorphous silica base stock is compressed into compacted bodies (also referred to as lumps) which are about 20–100% denser than the base stock. The compression of the dried silica base stock can be performed in accordance with conventional silica processing methods including compression via tandem rolls. The compressive forces applied to the silica can vary depending on the properties of the base stock, but enough force should be applied to produce a lump which will substantially maintain its physical integrity after the compressive forces are removed. This is determined by an attrition test in which the lumps exhibit less than 40% attrition. In order to obtain the desired bulk density, a deaeration may be performed (if necessary).

The lumps are then broken into smaller particles by any conventional means, with an attrition mill or a flake breaker being preferred. Granules of the preferred size are isolated through screening with appropriately sized screens. FIG. 1 shows a photomicrograph of a dye absorbing silica processed in the manner set forth above. The base stock utilized was a silica powder available under the mark Hubersil® 1714 from J. M. Huber Corporation of Edison, N.J. As can be seen from the photomicrograph, the dye absorbing silica granules have a non-spherical shape.

Silica granules obtained by the above mentioned compacting process do not require the addition of an organic binder (or any other binder) to hold them together. This is particularly advantageous as the presence of an organic binder has been shown to facilitate the growth of bacteria in the formulation into which the silica granules are incorporated. Further, binders often dissolve in the dentifrice thereby adversely affecting the integrity of the silica granules.

Examples of acceptable silica powders which can be processed into the dye absorbing silica granules of the present invention include powders available from J. M. Huber Corporation of Edison, N.J. under the marks Zeofree® 153, Zeodent® 165 and Hubersil® 1714. Some of the relevant physical properties of each of these silica powders are set forth in Table 1.

TABLE 1

| Base Silica | Zeofree ® 153* | Zeodent ® 165* | Hubersil ® 1714* |
|---|---|---|---|
| Oil absorption (cc/100 g) | 160–170 | 200–230 | 185–215 |
| Bulk Density (g/ml) | 0.20–0.22 | 0.13–0.16 | 0.14–0.18 |
| 5% pH | 6.5–7.5 | 6.5–7.5 | 6.0–6.8 |

*Zeofree, Zeodent and Hubersil are registered trademarks of J.M. Corporation of Edison, NJ.

As stated above, the dye absorbing silica of the present invention comprises silica granules which have a linseed oil absorption of at least about 150 cc/100 g, an average particle size of about 400 μm to about 600 μm, an attrition value of less than 30%, a bulk density of about 0.2 g/ml to about 0.6 g/ml, and a pH of about 6 to about 8. The particle size, linseed oil absorption, attrition value and bulk density were evaluated as follows:

Particle Size

Particle size was determined using a Horiba LA-910 particle size analyzer.

Linseed Oil Absorption

Oil absorption was determined by the rubout method. This method is based on the principle of mixing oil with a silica by rubbing with a spatula on a smooth surface until a putty-like paste is formed. The oil absorption value was obtained by measuring the quantity of oil required to have a paste mixture which will curl when spread out. The value represents the volume of oil required per unit weight of silica to saturate the silica sorptive capacity.

Calculation of the oil absorption value was done as follows:

Oil absorption=(cc oil absorbed/weight of silica)*100

Attrition Value

The attrition value was determined using a #800 Spex Mixer/Mill using 135 ml polystyrene Spex Mill jars, and −12+14 mesh ceramic beads. The procedure for determining the attrition the value is as follows: (1) 5.0 grams of silica granules are placed in the Spex Mill jar, 0.5 grams of the ceramic beads are then added to the jar and the entire contents of the jar are shaken on the Spex Mill for 5 minutes; (2) the contents of the jar are then placed on a 20 mesh screen which is positioned on top of an 80 mesh screen and a pan; (3) the screens are shaken by hand until all of the ceramic beads have been separated from the granules; (4) thereafter, the 20 mesh screen is separated from the 80 mesh screen and the 80 mesh screen is shaken by hand for about 30 seconds to separate the granules from the attrited powder, and (5) the granules are emptied from the 80 mesh screen onto a suitable weighing dish and the weight of the +80 mesh material is obtained by using a Mettler balance (0.01 grams accuracy). The % attrition=((5.00− weight of the +80 mesh material)/5.0)*100. The % attrition value should be good to +/−2% on repeat analysis.

Bulk Density

A 250 ml graduated cylinder was filled with the silica so that the silica was level with the top of the cylinder. The full cylinder was weighed and the weight of the granules was determined by subtracting the weight of the empty cylinder. The weight of the silica was divided by the standard volume (in ml) of the cylinder to provide the bulk density in (g/ml).

Visual Effect

The visual effect of the dye absorbing silica is another important property. The visual effect is controlled by the oil absorption of the starting (or base) silica powder, the % attrition of the compacted granules, and the particle size of the compacted granules. The visual effect is defined by the following equation:

visual effect=0.0089*(average particle size)+0.0032*(% attrition) +0.0000335*(oil absorption*average particle size) −0.00000104*(oil absorption*average particle size* % attrition)−3.137 where the average particle size is in microns, the % attrition is the value resulting from the attrition test described above and the oil absorption is in cc/100 g. The visual effect is rated on a scale of 0 to 10 with the dye absorbing speckles being invisible at 0 and being very visible at 10. It should be noted that at values of greater than 8, the mouth feel of the silica in a dentifrice is undesirable. The preferred range for the visual effect is from 2 to 8 and, more preferably, from 3 to 7.

Table 2 sets forth some relevant physical properties of several, preferred dye absorbing silicas prepared in the manner set forth above.

TABLE 2

| Silica Powder | Oil Absorption (cc/100 g) | Average Particle Size (microns) | % Attrition | Visual Rating |
|---|---|---|---|---|
| Zeodent ® 165 | 215 | 596 | 5 | 5 |
| Zeodent ® 165 | 215 | 514 | 7 | 5 |
| Zeofree ® 153 | 165 | 536 | 3 | 5 |
| Zeofree ® 153 | 165 | 454 | 8 | 3 |
| Hubersil ® 1714 | 200 | 519 | 6 | 5 |
| Hubersil ® 1714 | 200 | 513 | 10 | 4 |

Table 3 sets forth an example of a toothpaste formulation which incorporates the dye absorbing silica granules of the present invention.

TABLE 3

| Ingredients | Weight, grams |
|---|---|
| Glycerine, 99.5% pure | 11.637 |
| Sodium Carboxymethyl Cellulose | 0.7 |
| Polyethylene Glycol | 3.0 |
| Sorbitol, 70.0% | 42.07 |
| Deionized Water | 19.2 |
| Sodium Fluoride | 0.243 |
| Tetrasodium Pyrophosphate | 0.5 |
| Sodium Saccharin | 0.2 |
| Color Blue #1, 0.25% | 0.2 |
| Dye Absorbing Silica | 10.0 |
| Abrasive Silica | 10.0 |
| Titanium Dioxide | 0.4 |
| Sodium Lauryl Sulfate Powder | 1.2 |
| Flavor | 0.65 |
| Total Weight | 100.0 |

A preferred method of processing the ingredients set forth in Table 3 is as follows: the glycerine, sodium carboxymethyl cellulose, polyethylene glycol, and sorbitol are mixed together and stirred until the ingredients are dissolved to form a first admixture. The deionized water, sodium fluoride, tetrasodium pyrophosphate, and sodium saccharin are also mixed together and stirred until these ingredients are dissolved to form a second admixture. These two admixtures are then combined with stirring. Thereafter the color is added with stirring to obtain a "pre-mix."

The pre-mix is placed in a Ross mixer (Model 130 LDM) and the dye absorbing silica, abrasive silica and titanium dioxide are mixed without vacuum. A 30" vacuum is then drawn and the resultant admixture is stirred for approximately 15 minutes. Lastly, the sodium lauryl sulfate and the flavor are added and the admixture is stirred for approximately 5 minutes at a reduced mixing speed.

The dye absorbing silica of the present invention will absorb dyes, over time, found in almost any colored toothpaste or gel formulation. Examples of suitable dyes include Food Drug & Cosmetic (FD&C) dyes such as Blues Nos. 1 and 2, Reds Nos. 1, 2 and 3, and Yellow No. 5; Drug and Cosmetic (D&C) dyes such as Reds Nos. 2, 3, 6, 7, 8, 9, 10, 11, 12, 13, 19, 30, 31, 36 and 37, and Blue No. 1.

The dye absorbing silica absorbs and concentrates sufficient amounts of dye so that the resulting dentifrice formulation has a speckled appearance. The silica granules are darker in color relative to the dentifrice base thereby producing a visually appealing product.

It should also be noted that the addition of the dye absorbing silica of the present invention into toothpaste and gel formulations can increase the productivity for toothpaste manufacturers since the silica granules absorb liquids, over time, in the dentifrice formulations, in addition to the dyes contained therein. Accordingly, the toothpaste manufacturers can process a lower viscosity dentifrice since the dentifrice will thicken in the tube, as the water is absorbed, to a desired viscosity.

The present invention may be embodied in other specific forms without departing from the spirit or essential attributes thereof and accordingly reference should be made to the appended claims rather than to the foregoing specification as indicating the scope of the invention.

What is claimed is:

1. A dentifrice comprising, a humectant, a dental polishing agent other than a dye absorbing amorphous silica, a FD&C dye or pigment coloring agent, and dye absorbing amorphous silica granules, said dentifrice being a lightly colored dentifrice base containing titanium dioxide or a clear gel, said dye absorbing amorphous silica granules having a linseed oil absorption of at least about 150 cc/100 g and an average particle size of about 400 $\mu$m to about 600 $\mu$m, wherein said dye absorbing amorphous silica granules have absorbed a sufficient portion of said FD&C dye or pigment coloring agent from said dentifrice to be darker in color relative to said dentifrice base, thereby producing a speckled appearance in the dentifrice.

2. The dentifrice of claim 1 wherein said silica granules have a linseed oil absorption of about 165 cc/100 g to about 230 cc/100 g.

3. The dentifrice of claim 1 wherein said silica granules have an attrition value of less than 30%.

4. The dentifrice of claim 1 wherein said silica granules have a bulk density of about 0.2 g/ml to about 0.6 g/ml.

5. The dentifrice of claim 1 wherein said silica granules have a pH of about 6 to about 8.

6. The dentifrice of claim 1 wherein said silica granules comprise about 5.0% to about 15.0% by weight of said dentifrice.

7. The dentifrice of claim 1 wherein said silica granules have a visual effect of from about 3 to about 7.

8. The dentifrice of claim 1 wherein said silica granules have a non-spherical shape.

9. The dentifrice of claim 1 wherein said amorphous silica granules are substantially free of organic binder.

10. A dentifrice comprising, a humectant, a dental polishing agent other than a dye absorbing amorphous silica, a FD&C dye or pigment coloring agent, and dye absorbing amorphous silica granules, said dentifrice being a lightly colored dentifrice base containing titanium dioxide or a clear gel, said dye absorbing amorphous silica granules being devoid of organic binder and having a linseed oil absorption of at least about 150 cc/100 g and an average particle size of about 400 $\mu$m to about 600 $\mu$m, wherein said dye absorbing amorphous silica granules have absorbed a sufficient portion of said FD&C dye or pigment coloring agent from said dentifrice to be darker in color relative to said dentifrice base, thereby producing a speckled appearance in the dentifrice.

11. The dentifrice of claim 10 wherein said silica granules have a linseed oil absorption of about 165 cc/100 g to about 230 cc/100 g.

12. The dentifrice of claim 10 wherein said silica granules have an attrition value of less than 30%.

13. The dentifrice of claim 10 wherein said silica granules have a visual effect of from about 3 to about 7.

14. The dentifrice of claim 11 wherein said silica granules have aspherical shape.

15. A dentifrice comprising, a humectant, a dental polishing agent other than a dye absorbing amorphous silica, a FD&C dye or pigment coloring agent, and dye absorbing amorphous silica granules, said dentifrice being a lightly colored dentifrice base containing titanium dioxide or a clear gel, said dye absorbing amorphous silica granules having a linseed oil absorption of at least about 150 cc/100 g and an average particle size of about 400 $\mu$m to about 600 $\mu$m, wherein said dye absorbing amorphous silica granules being capable of absorbing said FD&C dye or pigment coloring agent from said dentifrice in an amount sufficient to be darker in color relative to said dentifrice base, thereby producing a speckled appearance in the dentifrice.

16. The dentifrice of claim 15 wherein said silica granules have a linseed oil absorption of about 165 cc/100 g to about 230 cc/100 g.

17. The dentifrice of claim 15 wherein said silica granules have an attrition value of less than 30%.

18. The dentifrice of claim 15 wherein said silica granules have a visual effect of from about 3 to about 7.

19. The dentifrice of claim 15 wherein said silica granules have aspherical shape.

20. The dentrifice of claim 15 wherein said amorphous silica granules are substantially free of organic binder.

* * * * *